(12) United States Patent
Weber

(10) Patent No.: US 6,848,456 B2
(45) Date of Patent: Feb. 1, 2005

(54) METHOD FOR DETERMINING THE EXISTENCE OF OBSTRUCTIONS IN THE PASSAGEWAYS OF A MEDICAL INSTRUMENT

(75) Inventor: Craig Weber, Chalfont, PA (US)

(73) Assignee: Custom Ultrasonics, Inc., Ivyland, PA (US)

( * ) Notice: Subject to any disclaimer, the term of this patent is extended or adjusted under 35 U.S.C. 154(b) by 16 days.

(21) Appl. No.: 10/341,172

(22) Filed: Jan. 13, 2003

(65) Prior Publication Data

US 2004/0134520 A1 Jul. 15, 2004

(51) Int. Cl.[7] ............................. B08B 3/02; B08B 9/027
(52) U.S. Cl. ................... 134/22.12; 134/18; 134/22.11; 134/22.18; 134/166 C; 134/166 R; 134/169 C; 134/171
(58) Field of Search .............................. 134/18, 22.11, 134/22.12, 22.18, 166 C, 166 R, 169 C, 171

(56) References Cited

U.S. PATENT DOCUMENTS 5,761,069 A 6/1998 Weber et al.
5,882,589 A * 3/1999 Mariotti ........................ 422/28
6,047,431 A * 4/2000 Canonica ............... 15/104.095

* cited by examiner

*Primary Examiner*—Zeinab El-Arini
(74) *Attorney, Agent, or Firm*—Caesar, Rivise, Bernstein, Cohen & Pokotilow, Ltd.

(57) ABSTRACT

A method for the reprocessing of a device having internal passageways by applying a fluid at a plurality of pressures to the internal passageways of the device to permit reuse of the device in a clean environment includes applying a fluid having a single input pressure to a pressure differentiation device having first and second pressure control fittings for providing first and second differing pressure outputs in accordance with the single input pressure and transmitting the fluid at the first and second differing pressures from the pressure differentiation device to the internal passageways. The internal passageways are reprocessed with the transmitted fluid at the first and second differing pressures, whereby the internal passageways are reprocessed at differing pressures in accordance with the single input pressure.

12 Claims, 8 Drawing Sheets

FIG.4A
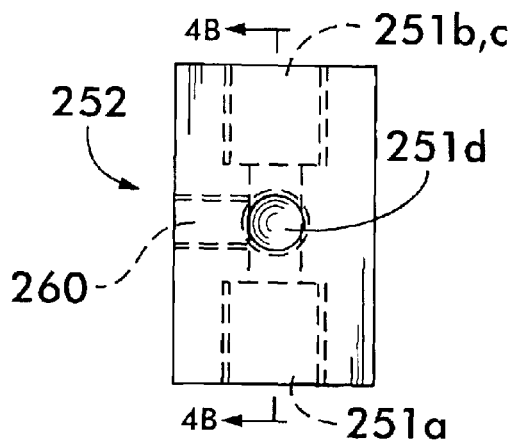
FIG.4B
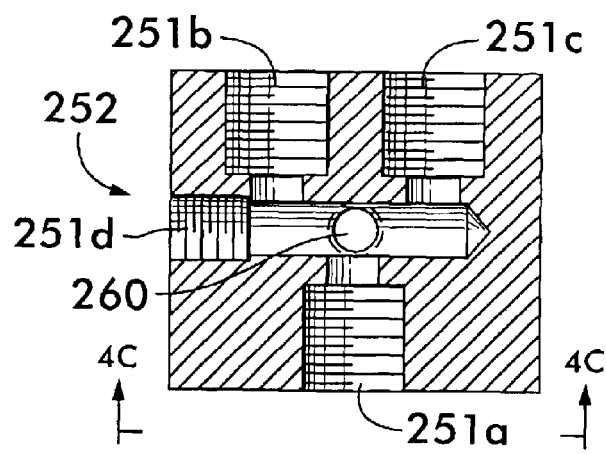
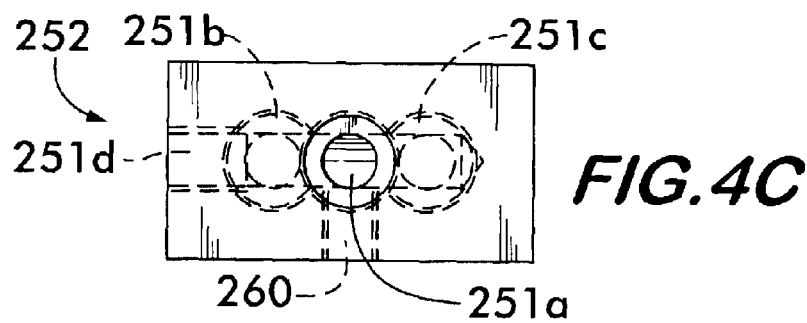
FIG.4C
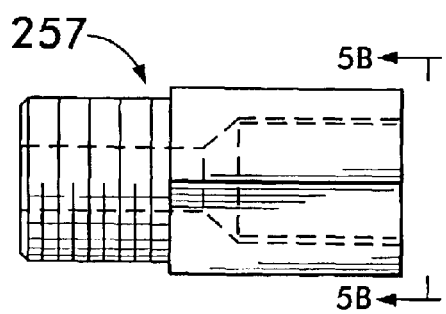
FIG.5A
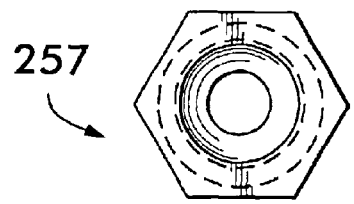
FIG.5B
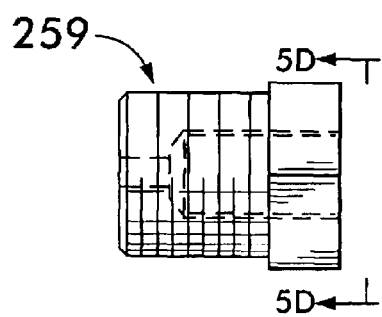
FIG.5C
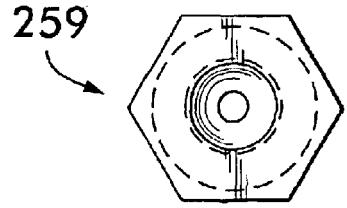
FIG.5D

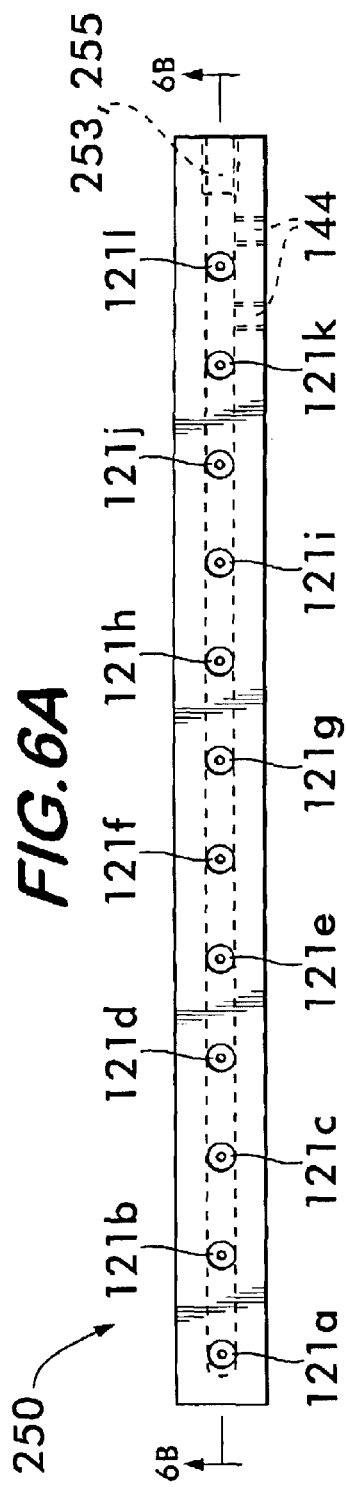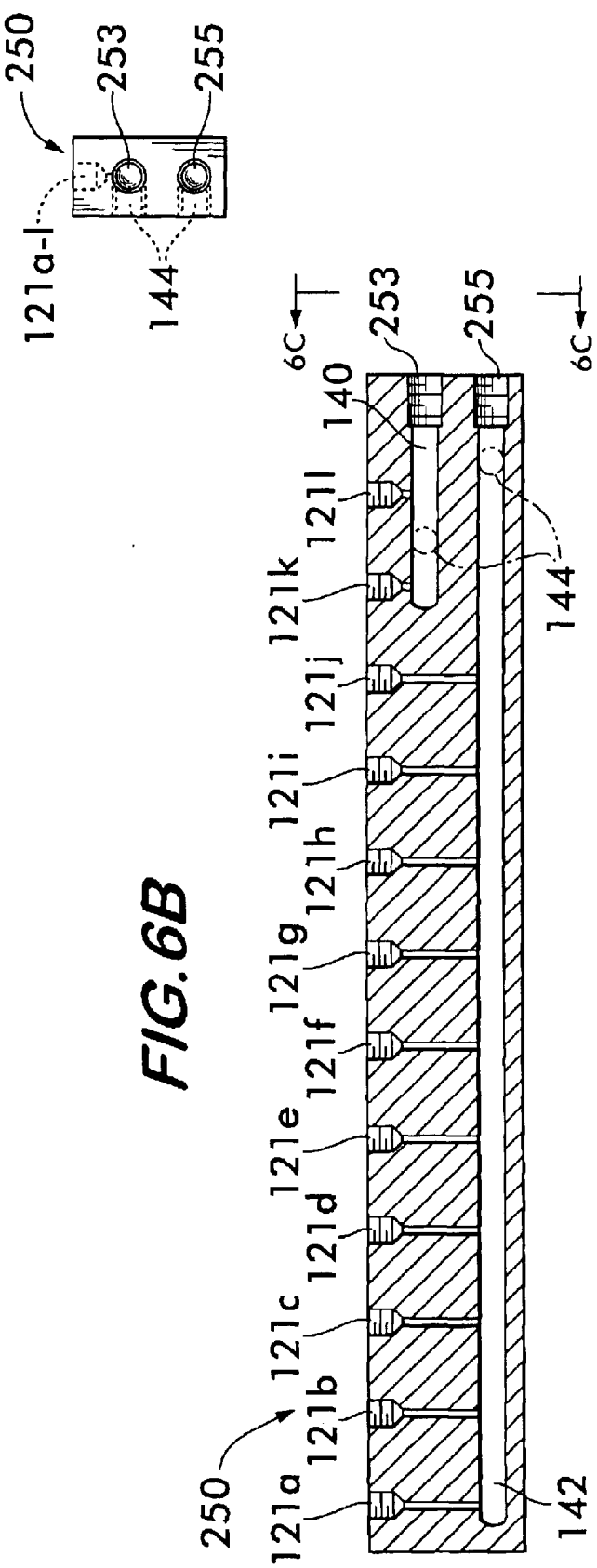
FIG.6A
FIG.6C
FIG.6B

METHOD FOR DETERMINING THE EXISTENCE OF OBSTRUCTIONS IN THE PASSAGEWAYS OF A MEDICAL INSTRUMENT

BACKGROUND OF THE INVENTION

Field of Invention

This invention relates generally to a method for the reprocessing of a contaminated device having internal passageways before such a device is reused in a clean environment. The term "reprocessing," as used herein constitutes the washing, disinfecting, sterilizing and/or pasteurizing of such a device. The term "device" as used herein constitutes any devices having internal passageways that require such reprocessing, including, but not limited to, medical instruments and medical devices. The terms "medical instrument" and "medical device" are understood to constitute devices having one passageway or a plurality of passageways, including, but not limited to endoscopes, colonoscopes, and other flexible and rigid medical instruments.

Some automated systems for reprocessing devices having internal passageways for reuse are generally available and are commonly relied upon. For example, systems for reprocessing medical instruments having passageways are used by hospitals to safeguard patients and hospitals employees from exposure to infection and cross-contamination. Such prior art reprocessing units are manufactured by several different companies including, Custom Ultrasonics, Inc., of Ivyland, Pa., the assignee of the present invention and application. For example there are reprocessing units in the prior art adapted for cleaning, disinfecting and sterilizing flexible scopes, e.g., upperand lower gastrointestinal scopes, colonoscopes and duodescopes.

Prior art reprocessing systems, suitable in particular for reprocessing medical instruments, operate in accordance with a predetermined protocol of reprocessing steps. The protocol is based upon the specific cleaning requirements of the particular instruments being cleaned. The reprocessing steps are precisely timed and sequenced in order to assure optimal results, based upon the correct combination of water temperature, detergent and chemical agents. Thus, parameters such as wash and rinse cycle time, chemical immersion cycle time and water temperature and pressure were preset by the reprocessing unit manufacturer and could not be altered by an end user of the system. U.S. Pat. No. 5,761,069, issued to Weber, et. al. teaches a system for cleaning medical instruments having a database of protocols corresponding to differing medical instruments for permitting a user to load and execute the protocol corresponding to the instrument being reprocessed.

An exemplary protocol for cleaning a medical instrument could include the following reprocessing steps, after the instrument has been placed in the cleaning basin of the reprocessing unit: (1) wash the internal and external surfaces of the instrument with a measured detergent-water mixture for a preset period of time; (2) activate ultrasonic crystals while washing; (3) drain the detergent-water mixture after the wash cycle is completed; (4) after draining, rinse the internal and external surfaces of the instrument with water at a preset temperature for a preset period of time; (5) introduce and circulate disinfectant over and through the instrument for a preset period of time; (6) drain the disinfectant from the wash basin; and (7) after draining of the disinfectant is complete, rinse the instrument with water; and (8) re-rinse the instrument with water.

Prior art reprocessing units adapted, in particular, for reprocessing medical equipment, typically comprise a variety of mechanical components, e.g., pumps, tubes, solenoid valves, ultrasonic transducers, heaters and probes that perform the various reprocessing steps. The pumps used in these units must be very precise and reliable over extended periods of time. Thus, pumps that are suitable for these units can be quite expensive.

In many cases it is necessary to reprocess devices having passageways of differing diameters. The differing diameters can occur in a single device having passageways of differing diameters, or in multiple devices, each having a single differing diameter. The presence of differing diameter passageways creates a need for fluid flows of corresponding differing pressures, because more narrow passageways require a higher pressure to force fluid therethrough. Prior art reprocessing units suitable for reprocessing devices having passageways of differing diameters included a plurality of pumps and associated tubing systems, wherein each pump provided one of the differing pressures required to reprocess the differing passageways of the devices.

Furthermore, some devices can have extremely narrow passageways, requiring dedicated high-pressure pumps that are capable of providing extremely high pressures. Pumps for such extremely narrow, high-pressure passageways have very low flow rates. Flow rates that are this low are difficult to monitor. For example, the flow rates of fluids through the passageways of some devices can be on the order of a drop a minute. Passageways this narrow can be found, for example, in flexible medical instruments, such as endoscopes.

Known reprocessing units are typically equipped with a pressure sensor for measuring the overall flow of fluid through the pump for the purpose of detecting obstructions in the passageways of the devices. However, is possible for an obstruction preventing flow of in one of the passageways to go undetected by the pressure sensor since the flow can continue through the remaining passageways and only the overall pressure of the liquid is determined.

Several governmental and independent agencies have issued guidelines for reprocessing particular types of medical instruments. For example, such guidelines often require that certain types of medical instruments be washed and sterilized using a chemical disinfectant, while other types of instruments need only be washed. The design of reprocessing units and the reprocessing steps they perform must conform to such guidelines. Additionally, guidelines have been created to reliably prevent instruments from being reused if an obstruction occurs in a single passageway of a plurality of passageways during reprocessing. Prior art reprocessing units are not reliably able to meet these guidelines.

SUMMARY OF THE INVENTION

A method for the reprocessing of a device having internal passageways by applying a fluid at a plurality of pressures to the internal passageways of the device to permit reuse of the device in a clean environment or patient safe environment includes applying a fluid having a single input pressure to a pressure differentiation device having first and second pressure control fittings for providing first and second differing pressure outputs in accordance with the single input pressure and transmitting the fluid at the first and second differing pressures from the pressure differentiation device to the internal passageways. The internal passageways are reprocessed with the transmitted fluid at the first and second differing pressures, whereby the internal passageways are reprocessed at differing pressures in accordance with the single input pressure. The first and second control fittings can be pressure fittings having respective first and second openings. The first and second control openings can have differing diameters. The pressure differentiation device can be a T-manifold.

A method for the reprocessing of a device having a plurality of internal passageways by applying a plurality of fluid channel flows to the internal passageways of the device to permit reuse of the device in a clean environment includes applying a pressurized fluid flow to the input of a manifold having a plurality of manifold outputs for forming a plurality of manifold output channel flows and transmitting the output channel flows of the plurality of output channel flows through respective flowmeters for measuring an individual flow rate for each of the output channel flows. Transmitting the measured output channel flows to the plurality of internal passageways and reprocessing the internal passageways using the output channel flows are also included. An obstruction in an internal passageway of the plurality of internal passageways is determined in accordance with a measured individual flow rate. The reprocessing of the device is aborted in accordance with the determining of the obstruction. An indication of which internal passageway of the plurality of internal passageways is obstructed is provided in accordance with a measured individual flow rate.

DESCRIPTION OF THE DRAWINGS

The features of this invention will become readily appreciated as the same becomes better understood by reference to the following detailed description when considered in connection with the accompanying drawings wherein:

FIGS. 4A–C show top, front and plan views of the pressure differentiation device of the reprocessing unit of FIG. 2.

FIGS. 5A–D are front and side views of the pressure control devices of the pressure differentiation manifold of FIGS. 4A–C.

FIGS. 6A–C show top, front and plan views of the pressure distribution manifold of the present invention.

DETAILED DESCRIPTION OF THE PREFERRED EMBODIMENTS

Figure 1:
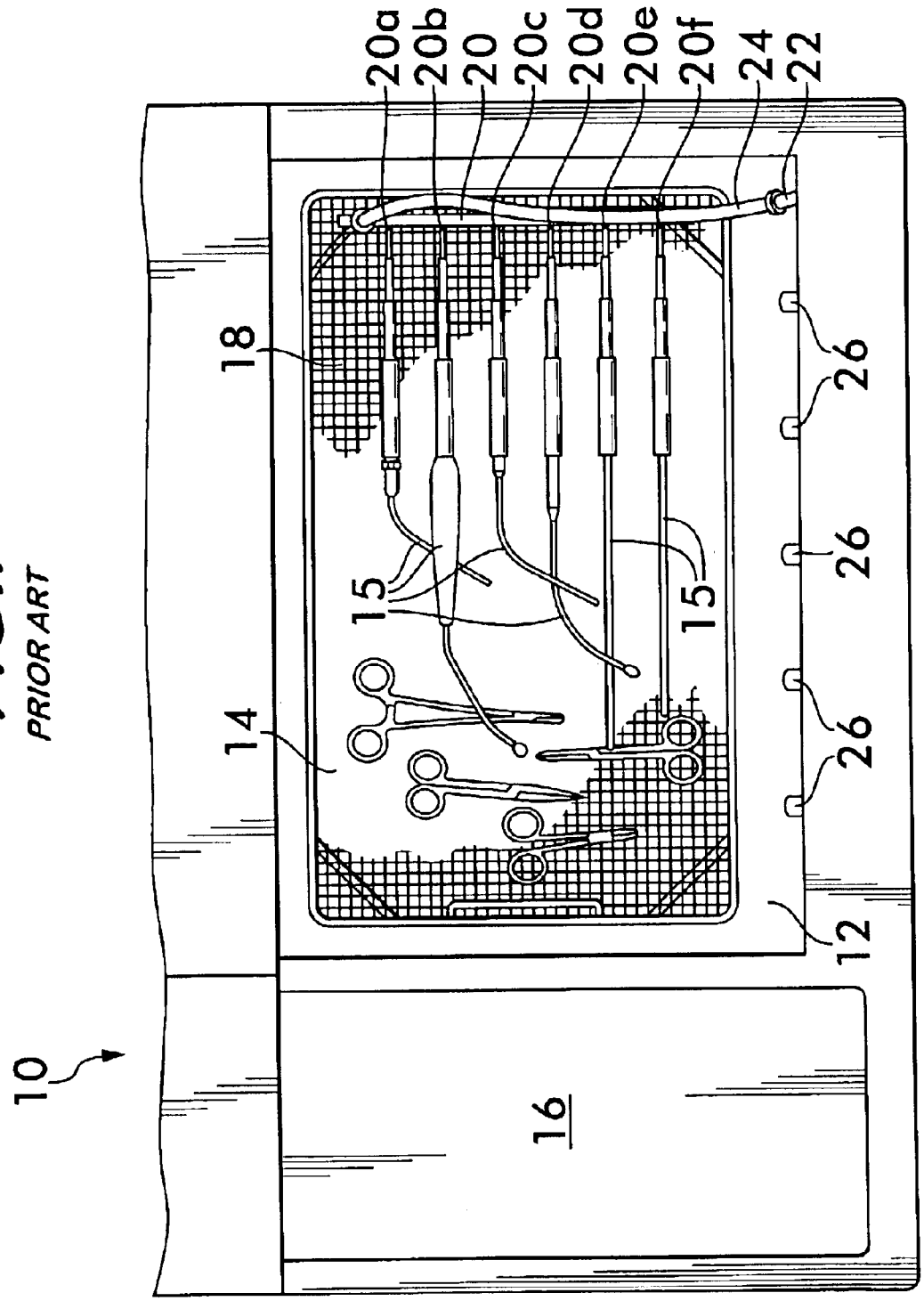
FIG. 1 is a top plan view of a prior art reprocessing unit wherein the cover of the reprocessing unit is disposed in an opened position to permit a view of a reprocessing basin containing devices to be reprocessed.

Referring now to the drawings, wherein like reference numerals refer to like parts, there are shown representations of reprocessing systems and methods suitable for using conventional reprocessing protocols to reprocess devices having internal passageways, such as medical instruments. An example of such a reprocessing protocol is disclosed in U.S. Pat. No. 5,761,069, issued to Weber, et. al., which is incorporated by reference herein.

FIG. 1 shows a top view of a prior art reprocessing unit 10, wherein a cover (not shown) is disposed in an open position. The reprocessing unit 10 includes a reprocessing basin 12, the instrument carrier 14, and a chemical disinfectant reservoir 16. The instrument carrier 14 is shown seated within the reprocessing basin 12. The instrument carrier 14 can be generally rectangular in shape and comprises a mesh-like bottom 18 which is arranged to hold the surgical instruments 15 during reprocessing, wherein the surgical instruments 15 each include a single passageway therethrough requiring reprocessing. The reprocessing basin 12 is also provided with a plurality of spray nozzles 26 for use during the rinse cycle.

The instrument carrier 14 includes a manifold assembly 20 having a plurality of ports 20a–f, each of which is shown applied to an internal passageway of a respective surgical instrument 15. In order to reprocess the surgical instruments 15 having a single passageway within the reprocessing unit 10, the surgical instruments 15 are disposed on the instrument carrier 14 for coupling to the ports 20a–f. Since the surgical instruments 15 have a single passageway, only a single one of the ports 20a–f is required for each surgical instrument 15. The manifold assembly 20 is connected to a port 22 by means of a tubing segment 24, which conducts fluid flow from the port 22 to the manifold assembly 20 for distribution by way of the ports 20a–f.

The fluid flow of the port 22 is driven by an oscillating pump (not shown). The oscillating pump operates to draw fluid, e.g., wash water, rinse water or chemical disinfectant, from the reprocessing basin 12, circulate that fluid through the ports 20a–f and the manifold assembly 20, and through the respective passageways of the surgical instruments 15 disposed on the instrument carrier 14, to effect the decontamination process during the wash, rinse and chemical immersion phases of the reprocessing protocol.

In this manner, the pressure delivered to each of the passageways of the surgical instruments 15 can be substantially equal in the reprocessing unit 10. Reprocessing unit 10 is thus suitable for reprocessing a plurality of surgical instruments 15 requiring such a single pressure to be applied to all of the passageways of the surgical instruments 15. However, many surgical instruments are provided with passageways of differing diameters. Such surgical instruments require differing pressures, corresponding to the differing diameters, for providing the required circulation of wash water, rinse water and chemical disinfectants through the passageways.

Figure 2:
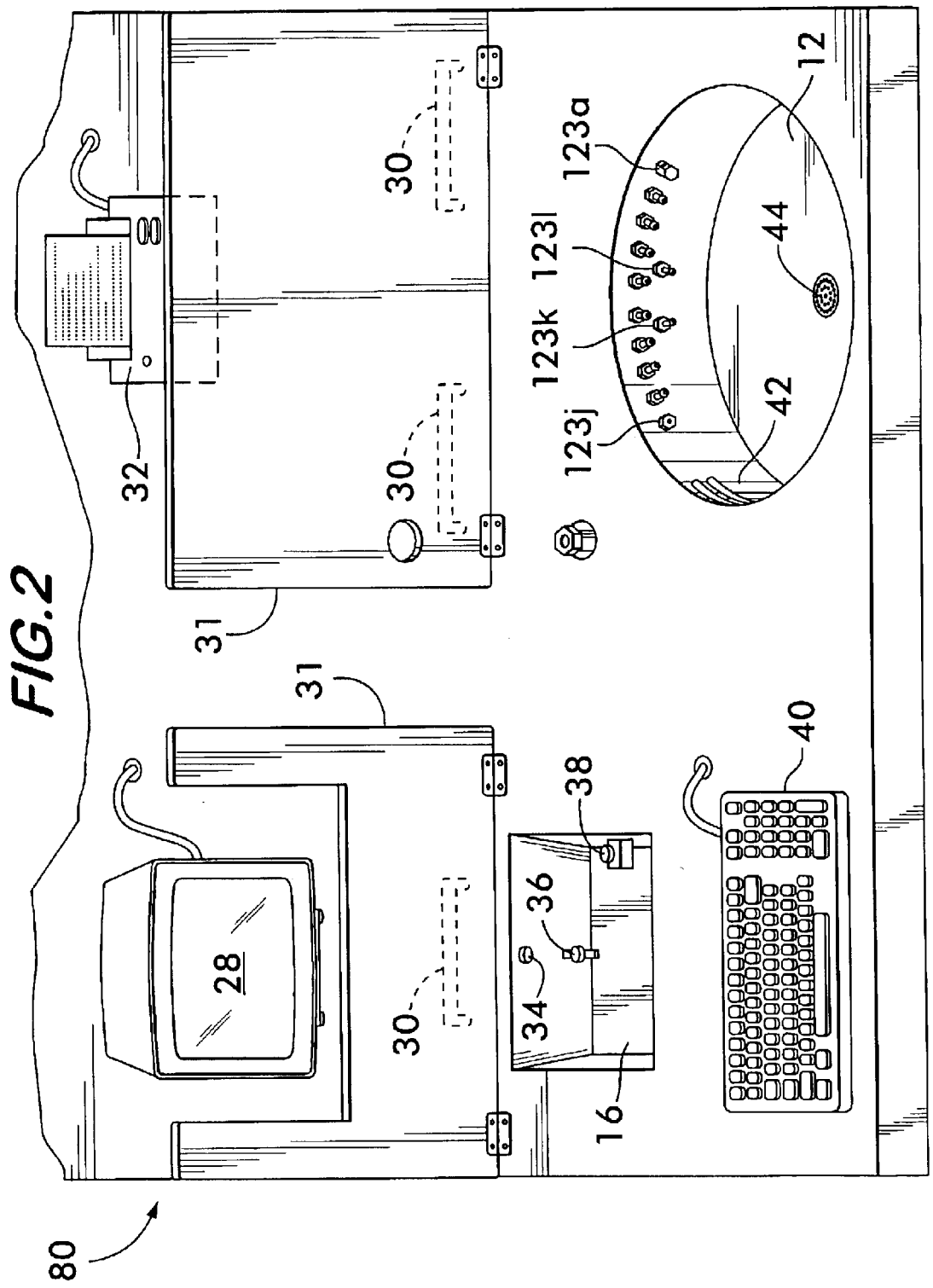
FIG. 2 is an elevational view of a reprocessing unit suitable for use with the system and method of the present invention.
Figure 3:
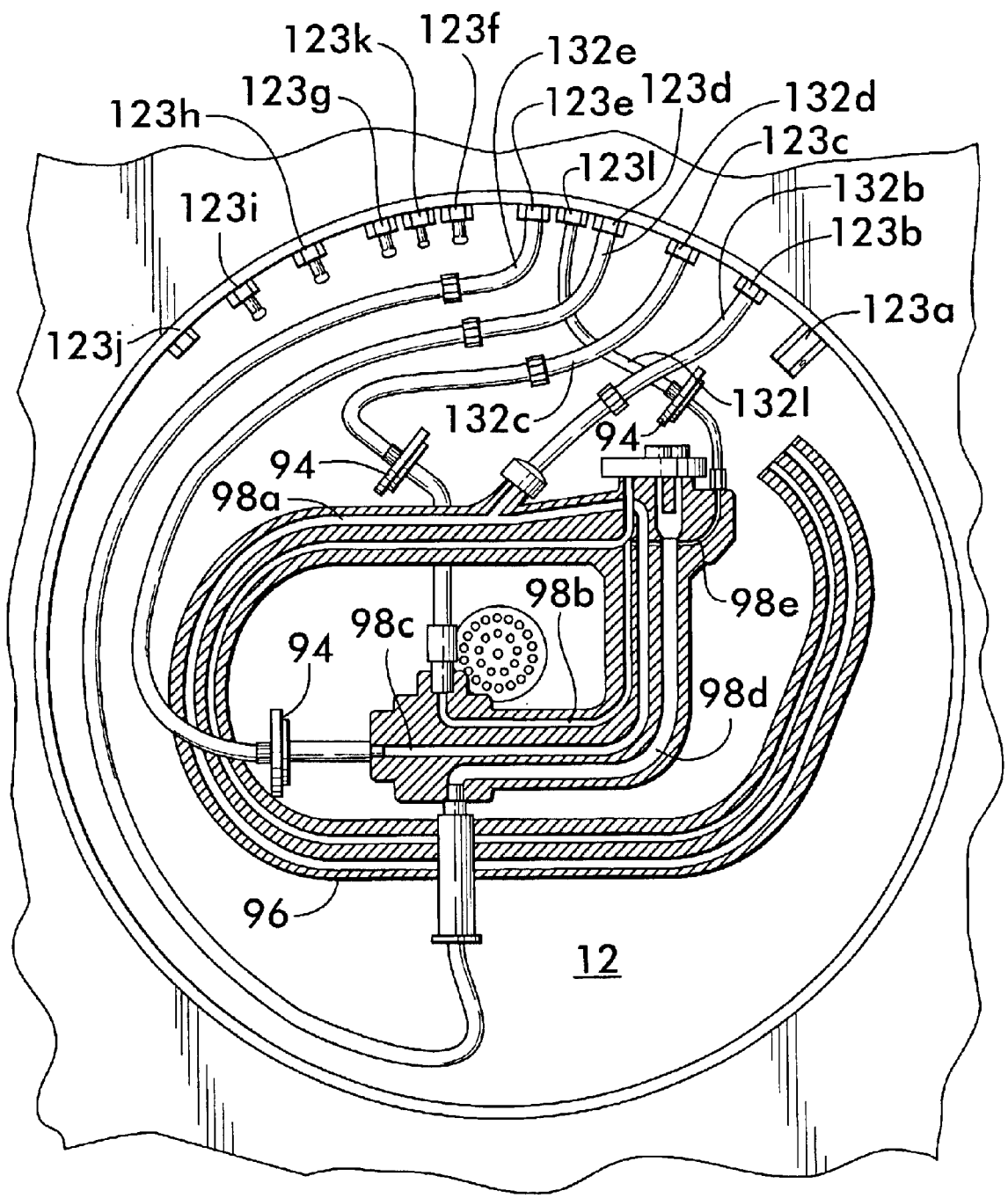
FIG. 3 shows a top view of the reprocessing basin of the reprocessing unit of FIG. 2 including a device to be reprocessed.

Referring now to FIGS. 2, 3, there is shown a reprocessing unit 80 suitable for use with the system and method of the present invention, and a view of a reprocessing basin 12 within the reprocessing unit 80. The reprocessing basin 12 holds a device 96 having internal passageways 98a–e for reprocessing of the device 96 by the reprocessing unit 80. In a preferred embodiment of the invention, the device 96 being reprocessed by the reprocessing unit 80 can be a medical instrument 96. In particular, the system and method of the invention are well suited for application to medical instruments including flexible scopes such as endoscopes that are used for upper and lower gastrointestinal studies.

The reprocessing unit 80 includes a keyboard 40, a monitor 28, a printer 32, and an associated personal computer (not shown) for permitting a user of the reprocessing unit 80 to communicate with and control the reprocessing unit 80. The reservoir 16 of the reprocessing unit 80 includes the sensors 34, 36, 38 for controlling devices such as a heater, a pump and a vacuum device (not shown) in order to protect against failure conditions such as overflow conditions in the reservoir 16. A removable door 42 within the reprocessing basin 12 covers additional sensors (not shown) for providing further operational capability and safety protection during the operation of the reprocessing unit 80. The door stops 30 are provided to stop the motion of the rotatable doors 31 covering the reservoir 16 and the reprocessing basin 12 when they are opened.

In the preferred embodiment, the reprocessing basin 12 can hold more than one device 96 upon a mesh for reprocessing of the internal passageways 98a–e thereof according to conventional reprocessing protocols. The reprocessing unit 80 is adapted to provide fluid flows of differing pressures to the device 96 or devices 96 being reprocessed when the internal passageways 98a–e have differing diameters. The reprocessing unit 80 is adapted to perform the multi-pressure reprocessing operations using a single pump (not shown), and to provide an indication of an obstruction in any of the internal passageways 98a–e of the device or devices 96 as described in more detail below. The single pump of the reprocessing unit 80 can be a diaphragm pump, an oscillating pump, or any other type of pump known to those skilled in the art.

The reprocessing basin 12 includes the supply ports 123a–l that can be selectively used to apply fluids at different fluid flow rates to the medical instruments 96 for reprocessing of the medical instruments 96. For example, the supply port 123j can be capped and reserved for use when needed. The supply port 123a can be used to blow off a fluid flow which is unusable due to difficulty in regulating and measuring their flow rates, as described in more detail below. In this example, at least the supply ports 123a–l that are not capped or blown off can be vented into the reprocessing basin 12 or coupled to the internal passageways 98a–e of a medical instrument 96 as needed.

For example, an internal biopsy passageway 98a of the medical instrument 96 can be coupled to the supply port 123b by way of the tubing segment 132b, and an internal water channel passageway 98b of the medical instrument 96 can be coupled to the supply port 123c by way of the tubing segment 132c. The internal passageway 98c can be coupled to the supply port 123d by way of the tubing segment 132d, and the internal suction passageway 98d can be coupled to the supply port 123e by way of the tubing segment 132e. The internal elevator water channel passageway 98e can be coupled to the supply port 123l by way of the tubing segment 132l.

The disk filters 94 and their tubing extensions can be disposed in line with the selected passageways 98a–e for preventing debris from reaching the medical instrument 96. For example, the disk filters 94 can be provided in the tubing segments 132c,d,e. The device for coupling the selected tubing segments 132a–l to the tubing extensions of the disc filters as shown can be the well known lure lock type of coupling. Typical diameters for some of the passageways 98a–e can be 0.508 millimeters to 4.8 millimeters.

Referring now to FIGS. 4A–C, there is shown a pressure differentiation device 252 for providing fluid flows of differing pressures from the output of a single conventional pump that provides a single pump output pressure. It is the different output pressures at the output of the pressure differentiation device 252 that are applied by way of the selected supply ports 123a–l to the internal passageways 98a–e of the medical instrument 96 for reprocessing the medical instrument 96 or any other device 96 having such passageways 98a–e. The single pump applied to the pressure differentiation device 252 can be a conventional diaphragm type pump, an oscillating pump, or any other type of pump known to those skilled in the art. The pressure differentiation device 252 can be a conventional T-manifold that is known to those skilled in the art.

The single pump output pressure is applied to the pressure differentiation device 252 at an input port 251a for application to the two output ports 251b,c of the pressure differentiation device 252. The output ports 251b,c threadably receive and secure different pressure control devices which can have openings of different diameters, as described in more detail below. The pressure control devices secured in the output ports 251b,c permit the pressure differentiation device 252 to provide two different pressures for the internal passageways 98a–e of the medical instruments 96. In the preferred embodiment the outport port 251b can be a high pressure output port and the output port 251c can be a low pressure output port.

In a typical embodiment of the invention, the higher pressure of the high pressure output port 251b of the pressure differentiation device 252 can be approximately 25 to 50 pounds per square inch. The lower pressure of the low pressure output port 251c can be approximately 2 to 20 pounds per square inch. The pressures at the output ports 251b,c can fluctuate within these ranges depending on factors such as the number of medical instruments 96 coupled to the reprocessing unit 80. It will be understood by those skilled in the art that a pressure differentiation device 252 having additional output ports with different pressure control devices can be used for reprocessing systems 80 requiring more than two differing pressures.

Referring now to FIGS. 5A–D, there are shown the pressure control devices 257, 259 of the pressure differentiation device 252 for providing the two different pressures to the internal passageways 98a–e of the medical instrument 96. The pressure control devices 257, 259 can be conventional pressure control orifice fittings 257, 259 that are threadably received and secured in the output ports 251b,c of the pressure differentiation device 252. The two different pressures are provided at the output ports 251b,c when a single pressure is applied to the input port 251a of the pressure differentiation device 252 because of the different diameters of the openings within the pressure control orifice fittings 257, 259. The pressure control orifice fitting 257 is a high pressure orifice fitting and the pressure control orifice fitting 259 is a low pressure orifice fitting.

In the preferred embodiment of the invention, the pressure differentiation device 252 can be formed with an entrance 260 for permitting an FDA approved liquid chemical sterilant as well as alcohol to be injected into the fluid stream passing through the device 252 for transmission through the selected supply ports 123a–l of the reprocessing basin 12 to the medical instruments 96. A disinfectant injection bulkhead communicating with the entrance 260 can be located on the exterior of the reprocessing unit 80 for convenience. Additionally, a filter (not shown) can be disposed in a conduit from the pump to the input port 251a of the device 252 for filtering fluid in transit to the internal passageways 98a–e. The filter can be, for example, a one-hundredth micron filter.

Referring now to FIGS. 6A–C, there are shown representations of the pressure distribution manifold 250 of the reprocessing unit 80, including the manifold input ports 253, 255, and the manifold output ports 121a–l. The pressure distribution manifold 250 can be a conventional air manifold understood by those skilled in the art. It is adapted to receive the fluid flows of the two different pressures from the output ports 251b,c of the pressure differentiation device 252 by way of the manifold input ports 253, 255. The fluid flows from the pressure distribution manifold 250 are applied by way of the manifold output ports 121a–l directly to the corresponding supply ports 123a–l of the reprocessing unit basin 12. Therefrom, they are selectively applied to the devices 96 such as the medical instruments 96. In the preferred embodiment, the manifold output ports 121a–j are low pressure ports and the manifold output ports 121k,l are high pressure ports.

A high pressure fluid flow is received at the high pressure manifold input port 253 of the pressure distribution manifold 250 from the orifice port 251b of the pressure differentiation device 252. A short longitudinal bore hole 140, opening at the high pressure manifold input port 253, is provided at one end of the pressure distribution manifold 250. The pressure distribution manifold 250 is bored transversely from each of the high pressure manifold output ports 121k,l to the longitudinal high pressure bore hole 140 in order to permit the high pressure output ports 121k,l to communicate with the high pressure bore hole 140. Thus, a high pressure fluid flow applied to the input port 253 of the pressure distribution manifold 250 is distributed to the high pressure, or narrower inner diameter, passageways of the medical instruments 96 by way of the high pressure bore hole 140 and the manifold output ports 121k,l.

A low pressure fluid flow is received at the low pressure input port 255 of the pressure distribution manifold 250 from the output port 251c of the pressure differentiation device 252. A long longitudinal bore hole 142, opening at the low pressure manifold input port 255, is provided within the pressure distribution manifold 250. Substantially as described with respect to the high pressure output ports 121k,l, transverse bore holes extending from the low pressure output ports 121a–j to the longitudinal low pressure bore hole 142 are provided. Thus, the low pressure manifold output ports 121a–j communicate with the low pressure bore hole 142. In this manner, a low pressure fluid flow applied to the low pressure input port 255 of the pressure distribution manifold 250 is distributed to the low pressure passageways of the medical instruments 96 byway of the low pressure bore hole 142 and the manifold output ports 121a–j.

Those skilled in the art will understand that possible turbulence at the distal end of the pressure distribution manifold 250, in the region of the manifold output port 121a can make the flow rates difficult to measure and/or difficult to control. Therefore, in the preferred embodiment of the invention, the fluid flows provided by way of the supply port 123a can be blown off into the reprocessing basin 12, rather than applied to a medical instrument 96.

The pressure measurement openings 144 on the side of the pressure distribution manifold 250 individually communicate with the longitudinal bore holes 140, 142. The presence of the pressure measurement openings 144 on the pressure distribution manifold 250 permits measurement of the pressures within the bore holes 140, 142, as described in more detail below.

Figure 7:
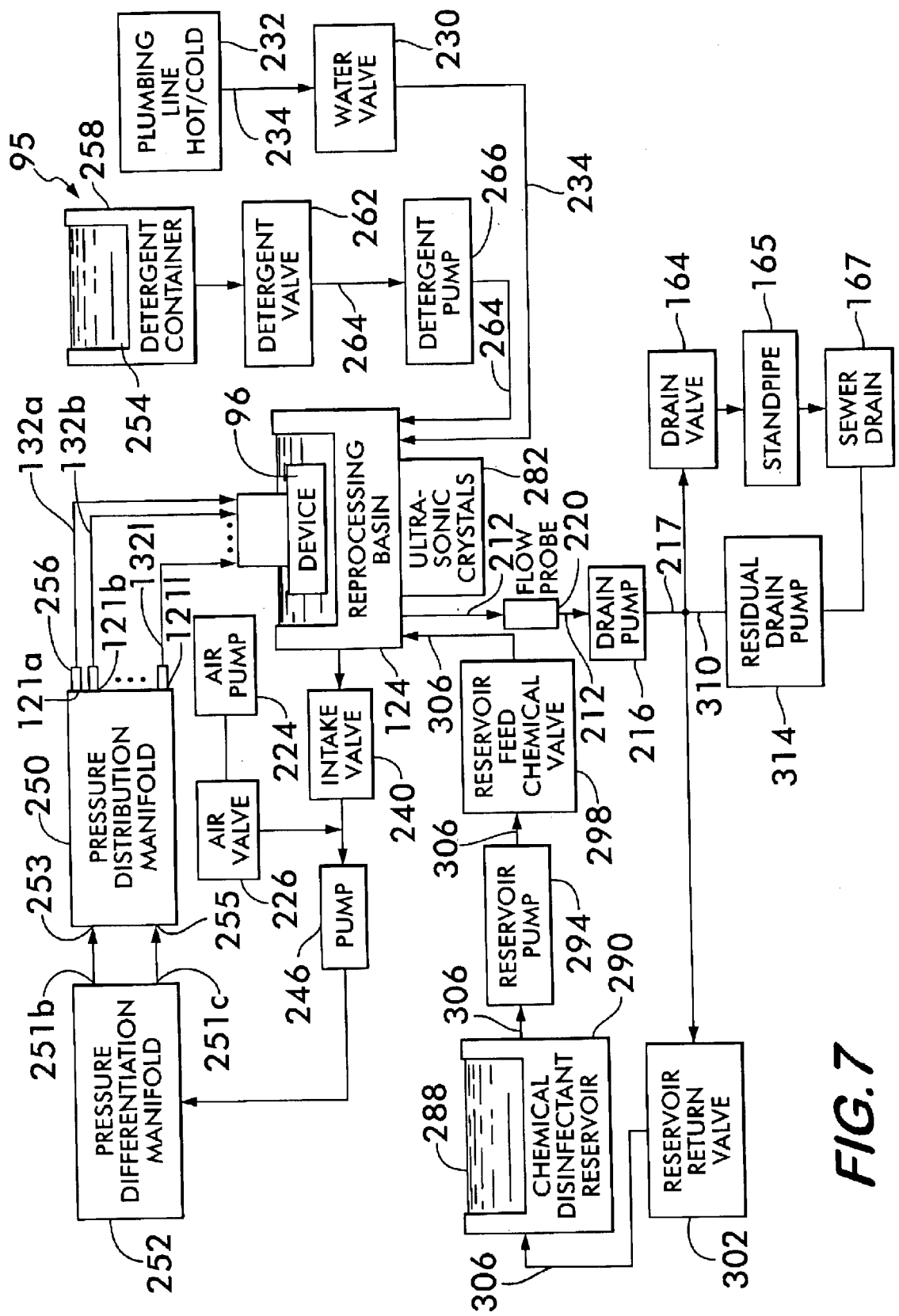
FIG. 7 shows a schematic block diagram illustrating the process flow of the operations performed by the reprocessing unit of FIG. 2.

Referring now to FIG. 7, there is shown a block diagram representation of a process flow 95 for performing a reprocessing protocol within the reprocessing unit 80 suitable for reprocessing devices such as the medical instruments 96.

During a fill step of the process flow 95, a solenoid-type water valve 230 is placed in an open position to enable water to flow from an outside hot/cold water source 232 through a water line 234, into the reprocessing basin 12 to immerse the medical instrument 96. The reprocessing basin 12 is provided with a drain 44 (shown in FIG. 2) located in the bottom of the reprocessing basin 12. The drain 44 is connected to a drain line 212. During the fill step, as wash water flows into the reprocessing basin 12 it begins to drain through the drain line 212. A drain valve 164, provided below the drain line 212 is normally in a closed state to prevent the draining of the water out of the system. This action enables the filling of the reprocessing basin 12.

A flow probe 220 is located adjacent the drain line 212 and is operative to detect the presence of liquid as wash water begins to fill the drain line 212 during filling of the reprocessing basin 12. Once the probe 220 detects the presence of moisture, the probe 220 sends a signal indicative thereof to a system controller which provides an indication to the user that the reprocessing basin 12 is filling with water. Additionally, an operational float (not shown) is located within the reprocessing basin 12. During filling, the operational float is buoyed upwardly and eventually reaches a predetermined height corresponding to a particular volume of wash water being present in the reprocessing basin 12. When the operational float reaches this predetermined level, the reprocessing unit 80 indicates to the user that the reprocessing basin 12 has been filled and that the washing step can begin. Thereafter, the water valve 230 is closed so that no additional wash water enters the reprocessing basin 12.

As wash water fills into the reprocessing basin 12 over the immersed medical instruments 96, a solenoid-type detergent valve 262 and a detergent pump 266 operate to withdraw a predetermined amount, e.g., three ounces, of detergent 254 from a detergent container 258 located adjacent the reprocessing unit 80 and inject the predetermined amount of detergent into the reprocessing basin 12 through a detergent line 264. The detergent 254 may be of any suitable composition. One particularly effective type of detergent is sold under the trademark TERGAL 800 by Custom Ultrasonics, Inc.

During the wash step, a pump 246, such as a diaphragm pump, is activated to draw the water/detergent mixture contained in the reprocessing basin 12 through an intake valve 240 and to circulate the mixture through the circular reprocessing basin 12, the output ports 121a–l of the pressure distribution manifold 250, the tubing segments 132a–l, and through the internal passageways 98a–e of the immersed medical instrument 96. Any unused output ports 121a–l can be blown off into the basin 12. The pump 246 is a single output pressure pump. In this manner fluid is recirculated through the immersed medical instrument 96 for a predetermined period of time in order to reprocess the internal passageways of the internal medical instrument 96 in accordance with a predetermined reprocessing protocol.

Figure 8A:
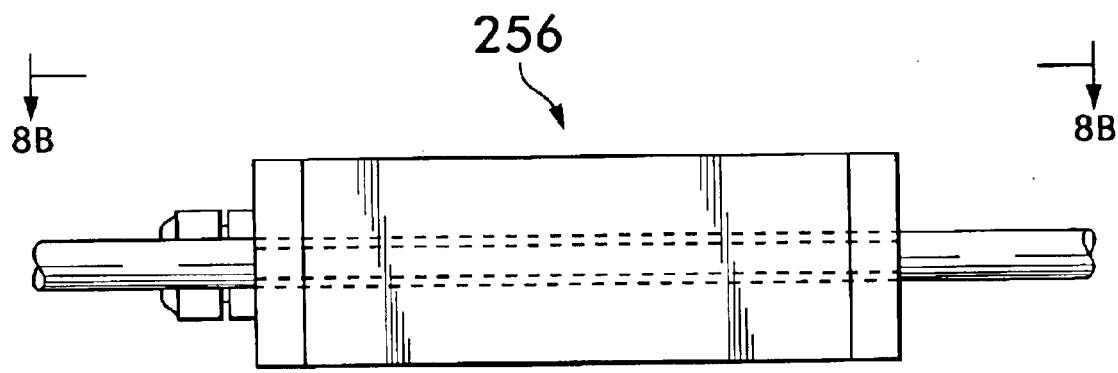
FIGS. 8A–B show top and front views of a flowmeter of the present invention.
Figure 8B:
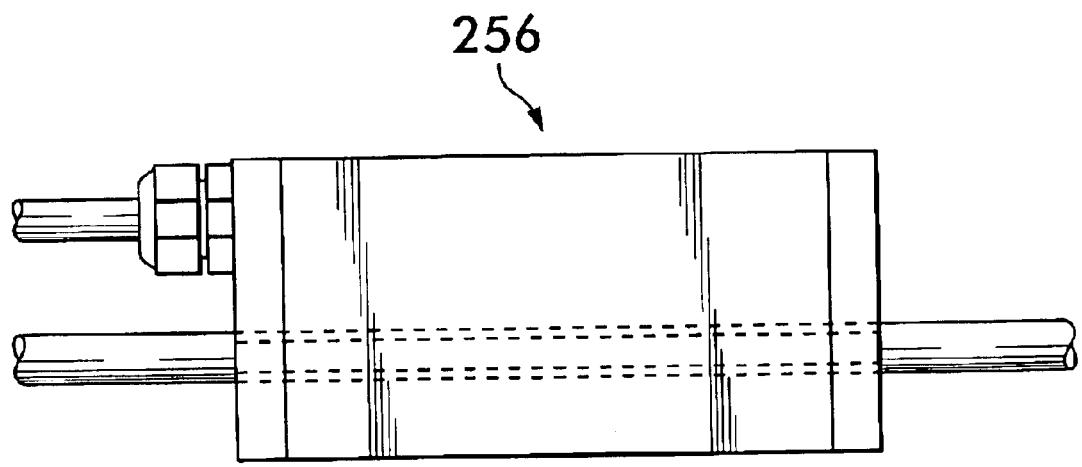

Referring now to FIGS. 8A–B, there is shown a flowmeter 256 for selectively coupling to the manifold output ports 121a–l and individually measuring the flow rates of the fluids within the manifold output ports 121a–l of the reprocessing unit 80 coupled thereto. The flowmeter 256 can be any conventional flow sensor suitable for measuring the flow rate through the ports 121a–l, and thereby through the tubing segments 132a–l. For example, the flowmeter 256 can be an in line straight-through flow tube sensor that uses ultrasonic sensing technology to measure the rate of flow of a fluid passing therethrough, such as the M-1500 Series provided by Malema Flow Sensors. The flowmeter 256 can be omitted from any unselected output ports 121a–l not supplying fluid to any internal passageways, for example the output ports 121a which is blown off into the reprocessing basin 12.

An ultrasonic sensing flowmeter 256 is preferred because it is non intrusive, thereby permitting the fluid flow to the internal passageways 98a–e of the medical instruments 96 to be measured without interference by the flowmeter 256. Ultrasonic sensing flowmeters 256 of this type are believed to be accurate from one-half cubic centimeter per minute to infinity for a multiple number of outputs.

The flowmeter 256 provides a flow rate signal according to the measured flow rate, for example by tripping a switch within the flowmeter 256 when the flow rate falls below a predetermined value.

In another embodiment of the invention, the flowmeters 256 can be of the well know piston type, wherein the force of the fluid flow through the flowmeter 256 raises and suspends a piston therein, until the flow rate falls below a predetermined value. When the flow rate falls below the predetermined value, the piston falls and a switch within the flowmeter 256 is tripped. The tripping of the switch within the flowmeter 256 indicates that the predetermined flow rate through the flowmeter 256 has not been maintained. It is believed that a flowmeter 256 of this type is not as accurate the ultrasonic type since it can interfere with the fluid flow being measured.

In one preferred embodiment of the invention, the minimum flow rate through the high pressure ports 121k,l can be approximately one cubic centimeter per minute. The minimum flow rate through the two lower pressure ports 121a,b at the distal end of the pressure distribution manifold 250 can be approximately fifty cubic centimeters per minute. The minimum flow rate through the remaining low pressure ports 121c–j can be 0.05 gallons per minute.

Thus, the flowmeters 256 disposed in line with the internal passageways 98a–e provide an indication to the user of the reprocessing system 80 when the flow through any of the passageways 98a–e of the surgical instruments 96 coupled to the reprocessing unit 80 is obstructed. When any of the internal passageways 98a–e is determined to be obstructed in this manner, the reprocessing operation set forth in the process flow 95 is aborted, and the abort condition is communicated to the user of the reprocessing unit 80. This feature prevents the inadvertent reuse of any device 96 that has not been completely reprocessed due to an obstruction in any of the internal passageways 98a–e being reprocessed. Without such a feature the operator can be left with a false sense of security regarding the success of the reprocessing operation.

In the preferred embodiment of the invention, individual indicator lights (not shown) corresponding to each flowmeter 256 coupled to the pressure distribution manifold 250 are mounted on the exterior of the reprocessing unit 80. The indicator lights permit an easy visual determination of which internal passageway 98a–e is obstructed when the reprocessing operation is aborted. Additionally, in one preferred embodiment of the invention, a lag time of approximately ten seconds can be provided between the detection of an obstruction by a flowmeter 256 and the abort of the reprocessing operation to allow for the breaking up of an obstruction due to back pressure provided by the pump.

Figure 9A:
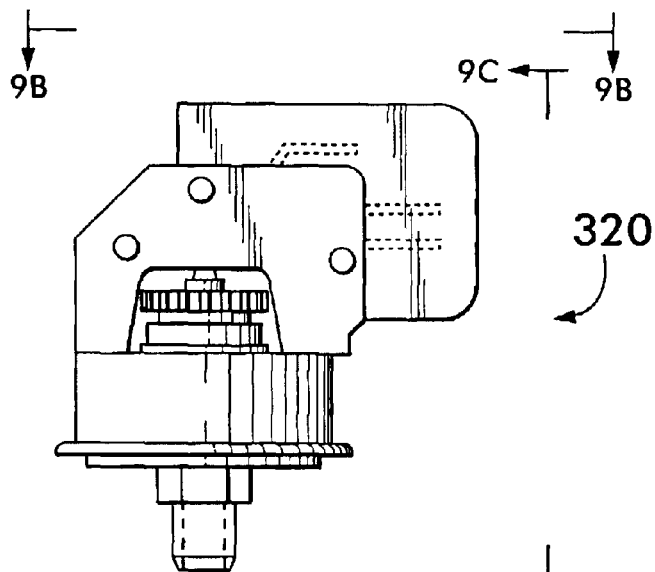
FIGS. 9A–C show top, front and plan views of a pressure sensor of the present invention.
Figure 9B:
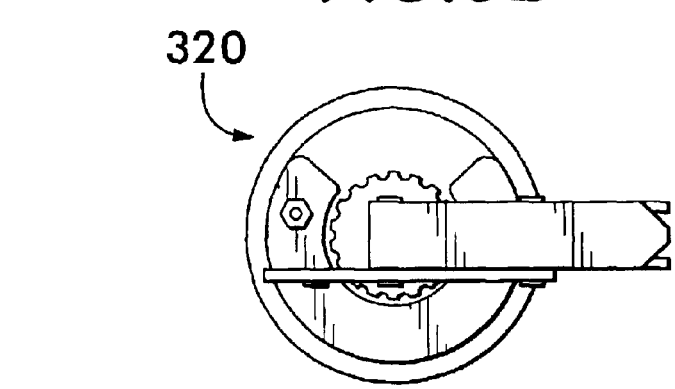
Figure 9C:
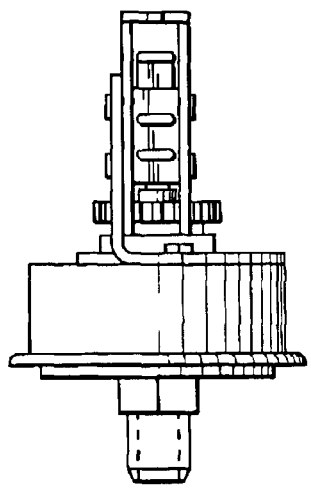

Referring now to FIGS. 9A–C, there are shown representations of the pressure sensing switch 320 of the reprocessing unit 80. The pressure sensing switch 320 is adapted to measure the pressure of the longitudinal bore holes 140, 142 within the pressure distribution manifold 250, and to provide an electrical pressure signal according to the measured pressure of the bore holes 140, 142.

In an alternate embodiment of the invention (not shown) a flowmeter 256 coupled to a manifold output port 121a–l of the pressure distribution manifold 250 can be omitted. In such an embodiment, the pressure sensing switch 230 is mounted in a pressure measurement opening 144 communicating with a longitudinal bore 140, 142 of the pressure distribution manifold 250. For example, the flowmeters 256 can be removed from the manifold output ports 121k,l, and the high pressure flow rate can be measured by a pressure sensing switch 320 mounted in the pressure measurement opening 144 disposed in communication with the longitudinal bore hole 140.

Thus, the pressure of the manifold output ports 121k,l is monitored using the pressure sensing switch 320 rather than measuring the fluid flow rate using a flowmeter 256. In this alternate embodiment, an obstruction within a high pressure passageway of the medical instrument 96 is detected by sensing a change in pressure rather than a change in flow rate. Thus, the reprocessing of the instrument 96 is aborted according to the pressure measured by the pressure sensing switch 320 rather than a direct measurement of flow rate. In one embodiment of the invention the pressure sensing switch 320 can be adapted to provide an electrical pressure signal when the measured pressure is at a level in the range of 1.5 to 15 psi.

In another alternate embodiment (not shown) of the reprocessing unit 80 an ultrasonic flow sensor such as the flowmeter 256 can be mounted on the pressure distribution manifold 250, for example, at the input end of the pressure distribution manifold 250. This type of ultrasonic measurement of flow rate is extremely sensitive, allowing the detection of changes in flow rate as small as a few drops per second. The reprocessing operations of the process flow 95 are aborted when the flow detected by such an ultrasonic measurement device mounted on the pressure distribution manifold 250 in this manner is below the predetermined level.

Once the water/detergent mixture has passed through the internal passageways 98a–e of the immersed medical instrument 96, it flows back into the reprocessing basin 12 where it is again recirculated by the pump 246 for a predetermined minimum period of time based upon guidelines provided by the detergent manufacturer, e.g., one-hundred eighty seconds. During the wash step, the ultrasonic crystals 282 located below the reprocessing basin are activated. When activated, the ultrasonic crystals 282 generate ultrasonic vibrations that act in combination with the detergent-water mixture to cause a cleansing action that breaks down, loosens and removes contaminants from the exterior and interior surfaces of the flexible medical instrument 96 to provide enhanced cleaning.

Once the predetermined time period for the wash step has elapsed, the drain step begins. During the drain step, the drain valve 164 is opened and the drain pump 216 is activated. While the pump 246 continues to pump the water/detergent mixture through the medical instrument 96, the mixture begins to drain out of the reprocessing basin 12 by means of the drain pump 216 which pumps the water/detergent mixture down the drain line 212 and into a T-assembly 217. The mixture travels through drain valve 164, through a standpipe 165 and into a sewer drain 167. Once the flow probe 220 detects the absence of moisture in the drain line 212, the drain pump 216 is shut off and the drain valve 164 is returned to its closed position.

After the drain pump 216 is shut off, an air pump 224 is activated and a solenoid-type air valve 226 is opened. By use of the air pump 224 forced air is directed through the pump 246, the manifold assembly 250, the tubing segments 132a–e, and through the internal channels of the medical instrument 96. The forced air acts to purge and clear away any residual water/detergent mixture remaining in the interior channels of the medical instrument 96. The purged residual water/detergent mixture flows down the drain line 212 located below the reprocessing basin 12 and collects in the bottom of the T-assembly 217 located below the drain line 212. The purged residual water/detergent mixture is removed from the bottom of the T-assembly 217 by means of a residual drain line 310 and a residual drain pump 314 that is activated simultaneously with the air pump 224.

The first rinse cycle comprises the steps of fill, rinse and drain steps. During the fill step, water is introduced into the reprocessing basin 12 from the outside source 232 by means of water valve 230 and water line 234. Since this is a rinse cycle, as opposed to a wash cycle, no detergent 254 is introduced during the fill step. During the rinse step of the process flow 95, the pump 246 draws the rinse water contained in the reprocessing basin 12 through the intake valve 240 and recirculates the rinse water for a predetermined minimum period of time in a manner as previously described above in connection with the wash step. Also, during the rinse step, the ultrasonic crystals 282 are activated.

Thereafter, the drain step begins. During the drain step, rinse water is pumped out of the reprocessing basin 12 by the drain pump 216. The water travels down the drain line 212 through the drain pump 216 and into the T-assembly 217. Because the drain valve 164 is in the opened position, the water travels through drain valve 164 and through standpipe 165 and into a sewer drain 167.

Once the flow probe 220 detects the absence of moisture in the drain line 212, the drain pump 216 is shut off. Some residual water remains in the bottom of the T-assembly 217 that cannot be removed by the drain pump 216. This residual rinse water is removed from the bottom of the T-assembly 217 by means of the residual drain line 310 and the residual drain pump 314 in the manner previously described. By removing all residual rinse water from the T-assembly 217, chemical disinfectant introduced in the next step of the protocol will not become diluted with any residual rinse water.

Once the drain step 141 is complete and all residual rinse water has been removed from the T-assembly 217, the next fill step begins and a chemical disinfectant 288 is introduced into the reprocessing basin 12. One particularly effective type of chemical disinfectant is 2% or 3% glutaraldehyde which is marketed by a number of different companies under various brand names such as Cidex manufactured by Johnson & Johnson. The introduction of the disinfectant 288 is effected by opening a reservoir feed valve 298 to cause a reservoir pump 294 to pump the chemical disinfectant 288 from a chemical disinfectant reservoir 290 through a chemical line 306 into the reprocessing basin 12. The chemical disinfectant 288 enters and fills the reprocessing basin 12 to a predetermined height as previously described.

Once the reprocessing basin 12 has been filled with the chemical disinfectant 288 to the predetermined level, the pump 246 is activated to draw the chemical disinfectant 288 contained in the reprocessing basin 12 through the intake valve 240. This action circulates the chemical disinfectant 288 through the ports of the manifold 250, the tubing segments 132a–e and through the internal passageways 98a–e of the immersed medical instrument 96. Once the chemical disinfectant 288 has passed through the internal passageways of 98a–l of the immersed medical instrument 96, it flows back into the reprocessing basin 12 where it is recirculated by the pump 246 for a predetermined minimum period of time based upon guidelines provided by the manufacturer of the chemical disinfectant 288. Once the predetermined minimum time period for the chemical immersion step has elapsed, the pump 246 is turned off.

Thereafter, the chemical disinfectant 288 is returned to the chemical disinfectant reservoir 290 for reuse. To enable the return of the chemical disinfectant 288 to the reservoir 290, the drain valve 164 is closed and the reservoir return valve 302 is opened. The drain pump 216 is activated and the chemical disinfectant 288 is pumped through the chemical line 306, through the reservoir return valve 302 and back into the chemical reservoir 290. Once the flow probe 220 detects the absence of moisture in the drain line 212, the drain pump 216 is tuned off. Thereafter, two additional rinse cycles are performed. The first rinse cycle comprises a first rinse and a drain phase. The rinse cycle is performed in a manner similar to the rinse cycle previously described. However, this rinse cycle does not include use of the residual drain line 310 and residual drain pump 314. The ultrasonic crystals 282 are activated during the rinse step of this rinse cycle.

The second rinse cycle comprises fill, second rinse and drain phases. This rinse cycle is performed in a manner similar to the rinse cycle previously described, i.e., fill, rinse and drain phases, and includes use of the residual drain line 310 and residual drain pump 314. The ultrasonic crystals 282 are activated during the rinse step of this rinse cycle. Once this rinse cycle has been completed, the reprocessing protocol is complete and the instrument may be removed from the reprocessing chamber for reuse.

Without further elaboration, the foregoing will so fully illustrate the invention that others may, by applying current or future knowledge, readily adapt the same for use under the various conditions of service.

What is claimed is:

1. A method for the reprocessing of a device having a plurality of internal passageways by applying a plurality of fluid channel flows to said internal passageways of said device to permit reuse of the device in a clean environment, the method comprising the steps of:

(a) applying a pressurized fluid flow to an input of a manifold having a plurality of manifold outputs for forming a plurality of manifold output channel flows;

(b) transmitting each of the manifold output channel flows of said plurality of manifold output channel flows through a respective flowmeter for measuring an individual flow rate for each of said manifold output channel flows to provide measured output channel flows;

(c) transmitting said measured output channel flows to said plurality of internal passageways;

(d) reprocessing said internal passageways using said measured output channel flows; and (e) determining an obstruction in an internal passageway of said plurality of internal passageways in accordance with a measured individual flow rate.

2. The method for the reprocessing of a device of claim 1, further comprising the step of aborting said reprocessing of said device in accordance with the determining of step (e).

3. The method for the reprocessing of a device of claim 2, further comprising the steps of determining and indicating which internal passageway of said plurality of internal passageways is obstructed in accordance with said measured individual flow rate.

4. The method for the reprocessing of a device of claim 1, wherein said device comprises a medical instrument.

5. The method for the reprocessing of a device of claim 4, further comprising the further step of measuring said output channel flows using a non-intrusive flow measuring device.

6. The method for the reprocessing of a device of claim 5, wherein said non-intrusive flow measuring device is an in-line flow through sensor.

7. The method for the reprocessing of a device of claim 6, wherein said non-intrusive device is an ultrasonic measuring device.

8. The method for the reprocessing of a device of claim 6, further comprising the step of measuring an output channel flow by means of a pressure measuring device.

9. The method for the reprocessing of a device of claim 4, wherein step (e) comprises the further step of determining said obstruction in accordance with a predetermined minimum flow rate.

10. The method for the reprocessing of a device of claim 9, wherein said plurality of manifold output channel flows includes first and second output channel flows having corresponding first and second differing pressures for reprocessing said internal passageways at said first and second differing pressures.

11. The method for the reprocessing of a device of claim 10, further comprising the steps of transmitting said first and second output channel flows through respective first and second flowmeters for detecting an obstruction in accordance with first and second differing minimum flow rates.

12. The method for the reprocessing of a device of claim 10, further comprising the step of applying a single pump pressure to a pressure differentiation device to provide said differing pressures.

* * * * *